(12) United States Patent
Kwong et al.

(10) Patent No.: US 9,766,367 B2
(45) Date of Patent: Sep. 19, 2017

(54) TRIPLE PHASE EVALUATION OF FORMATION FLUIDS

(71) Applicant: Halliburton Energy Services, Inc., Houston, TX (US)

(72) Inventors: KwokShan Kwong, Houston, TX (US); Weijun Guo, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/429,298

(22) PCT Filed: Nov. 16, 2012

(86) PCT No.: PCT/US2012/065523
§ 371 (c)(1),
(2) Date: Mar. 18, 2015

(87) PCT Pub. No.: WO2014/077833
PCT Pub. Date: May 22, 2014

(65) Prior Publication Data
US 2015/0241595 A1    Aug. 27, 2015

(51) Int. Cl.
*G01V 5/10* (2006.01)
*G01N 33/24* (2006.01)
*E21B 49/08* (2006.01)

(52) U.S. Cl.
CPC ............. *G01V 5/10* (2013.01); *E21B 49/087* (2013.01); *G01N 33/241* (2013.01); *G01V 5/102* (2013.01)

(58) Field of Classification Search
CPC ... G01V 5/00; G01V 5/10; G01V 9/00; G01V 5/102; G01N 33/241; E21B 49/087
See application file for complete search history.

(56) References Cited

U.S. PATENT DOCUMENTS

| | | | |
|---|---|---|---|
| 3,942,004 A | 3/1976 | Kehler | |
| 4,326,129 A | 4/1982 | Neufeld | |
| 7,372,018 B2 | 5/2008 | Trcka | |
| 7,566,869 B2 | 7/2009 | Riley et al. | |
| 2007/0023626 A1* | 2/2007 | Riley | G01V 5/101 250/269.6 |
| 2008/0114547 A1 | 5/2008 | Syngaevsky | |

(Continued)

FOREIGN PATENT DOCUMENTS

| WO | WO-2010/135618 A2 | 11/2010 |
|---|---|---|
| WO | WO-2011/086145 A1 | 7/2011 |
| WO | WO-2014077833 A1 | 5/2014 |

OTHER PUBLICATIONS

"International Application Serial No. PCT/US2012/065523, Response filed Aug. 21, 2014 to Written Opinion mailed May 3, 2013", 2 pgs.

(Continued)

*Primary Examiner* — David Porta
*Assistant Examiner* — Faye Boosalis
(74) *Attorney, Agent, or Firm* — Gilliam IP PLLC (57) ABSTRACT

Various embodiments include apparatus and methods to conduct a triple phase evaluation of a formation. The evaluation can be performed using a pulsed-neutron tool including a long detector and a detector to make sigma measurements. Additional apparatus, systems, and methods are disclosed.

16 Claims, 5 Drawing Sheets

(56) References Cited

U.S. PATENT DOCUMENTS

2010/0228483 A1    9/2010   Lecompte
2012/0068060 A1    3/2012   Chace et al.

OTHER PUBLICATIONS

"International Application Serial No. PCT/US2012/065523, International Preliminary Report on Patentability mailed Mar. 4, 2015", 7 pgs.

"International Application Serial No. PCT/US2012/065523, International Search Report mailed May 3, 2013", 3 pgs.

"International Application Serial No. PCT/US2012/065523, Written Opinion mailed May 3, 2013", 6 pgs.

"Austrailian Application Serial No. 2012394402, First Examiner Report mailed Mar. 22, 2016", 2 pgs.

* cited by examiner

Fig. 1

| Solids | | | Fluids | | | |
|---|---|---|---|---|---|---|
| Matrix | Dry Clay | Clay Bound Water | Cap-held Water | Free-Water | Oil | Gas |

Fig. 2A

| Matrix | Dry Clay | Clay Bound Water | Liquids | Gas |
|---|---|---|---|---|
| Vmatrix | Vshale | | Effective Porosity (EFFPOR) | |
| | | Total Porosity (TOTPOR) | | |
| | | | | Sg Gas Saturation (SATG) |
| | | | | Vg |

Fig. 2B

| Matrix | Dry Clay | Clay Bound Water | Water | Oil | Gas |
|---|---|---|---|---|---|
| Sigma Matrix | ShaleMatrix | | Sigma Water | Sigma Oil | Sigma Gas |
| Vmatrix | Vshale | | Vwater | Voil | Vg |

TRIPLE PHASE EVALUATION OF FORMATION FLUIDS

PRIORITY APPLICATIONS

This application is a U.S. National Stage Filing under 35 U.S.C. 371 from International Application No. PCT/US2012/065523, filed on 16 Nov. 2012, and published as WO2014/077833 A1 on 22 May 2014, which applications and publication are incorporated herein by reference in their entirety.

TECHNICAL FIELD

The present invention relates generally to apparatus and methods of making and evaluating measurements.

BACKGROUND

In drilling wells for oil and gas exploration, understanding the structure and properties of the associated geological formation provides information to aid such exploration. Measurements in a borehole are typically performed to attain this understanding. Measurements may include performing neutron measurements to determine properties of material phases in the formation under investigation. Further, the usefulness, efficiency, and accuracy of traditional measurements may be related to the precision or quality of the techniques to attain and process data derived from such measurements.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

Figure 1:
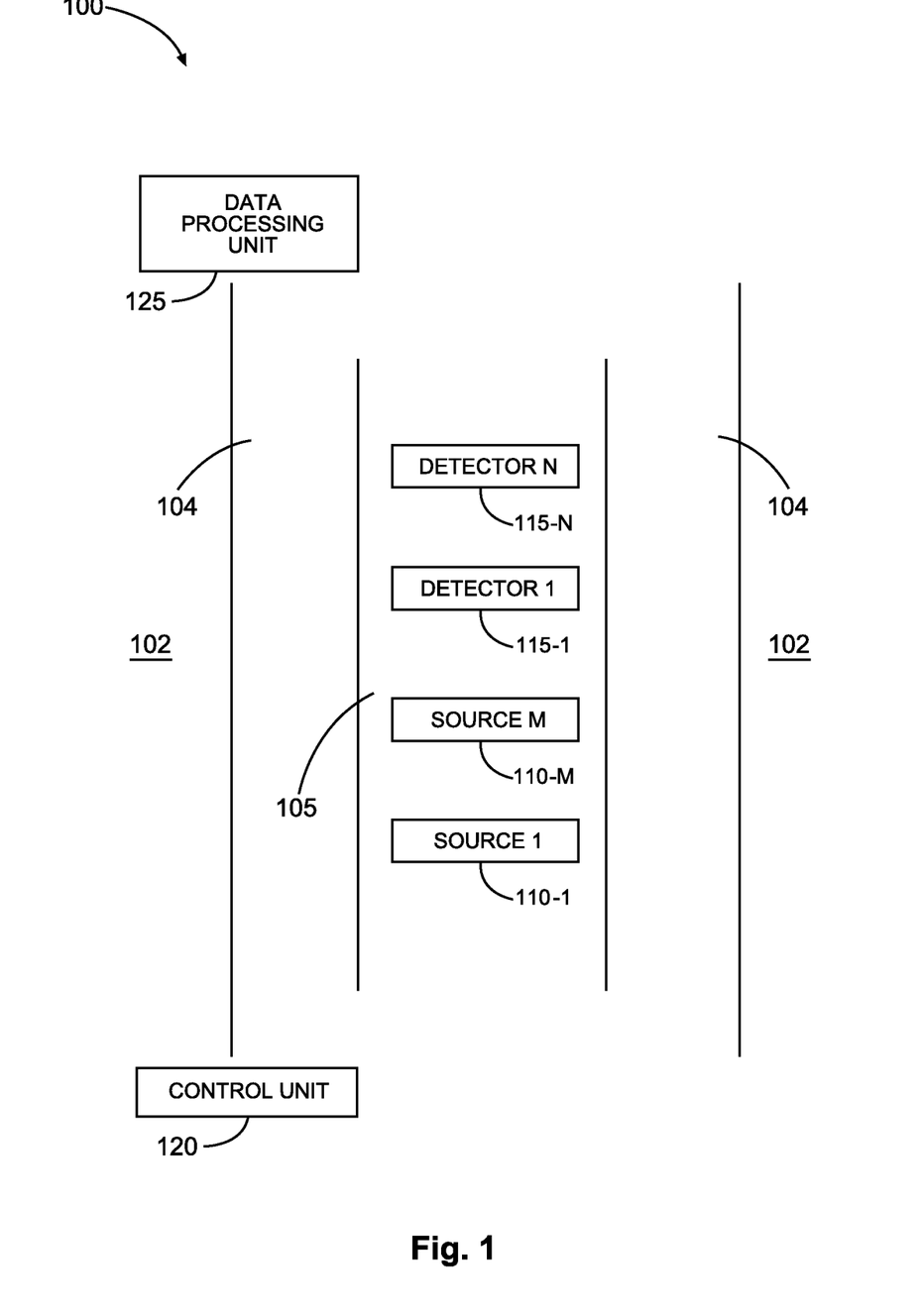
FIG. 1 illustrates an example system having a multi-detector pulsed-neutron tool, in accordance with various embodiments.

FIG. 1 shows an example of an embodiment of a system 100 having a multi-detector pulsed-neutron tool 105. The pulsed-neutron tool 105 can include a number of neutron sources 110-1 . . . 110-M and a number of detectors 115-1 . . . 115-N, where the pulsed-neutron tool 105 is deployable in a borehole 104 to make measurements of a formation 102. The detectors 115-1 . . . 115-N can include one or more long detectors. A long detector can be realized as neutron-gamma detectors, neutron-neutron detectors, or combinations thereof that have a source to detector spacing greater than 26 inches. The system 100 can include instrumentality to make inelastic counts and capture counts of neutron-induced gamma rays and to generate ratios of inelastic counts to capture counts.

The instrumentality can include a control unit 120 and a data processing unit 125. The control unit 120 and the data processing unit 125 may be integrated with each other. The control unit 120 and the data processing unit 125 may be integrated with the pulsed-neutron tool 105 operable downhole. The control unit 120 and the data processing unit 125 may have distributed components. Distributed components may include components downhole in the vicinity of the pulsed-neutron tool 105 deployed for operation and components at the surface or at locations between the surface and the vicinity of the operational pulsed-neutron tool 105.

In various embodiments, a formation evaluation method can be performed to analyze the multi-phase fluids in rocks using a triple phase evaluation. Multi-detector pulsed pulsed-neutron tools can be used to make measurements for the evaluation. Long detector measured inelastic and captured counts and their ratios can be characterized for gas phase evaluation. The triple phase evaluation can include sigma or capture count decay rates combined with the long detector measurements to evaluate water and oil phases.

Figure 2A:
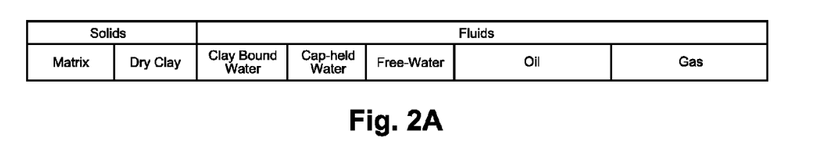
FIGS. 2A-2C show petrophysical models including a classical model, a two phase model related to a long detector measurement, and a three phase model related a long detector measurement, in accordance with various embodiments.
Figure 2B:
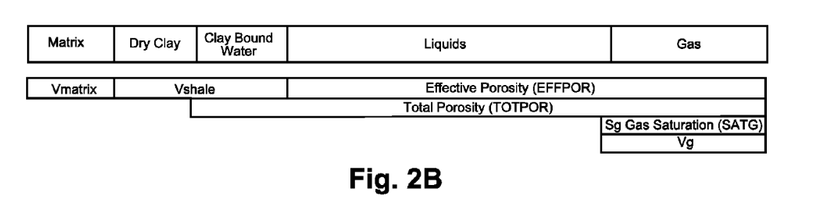
Figure 2C:
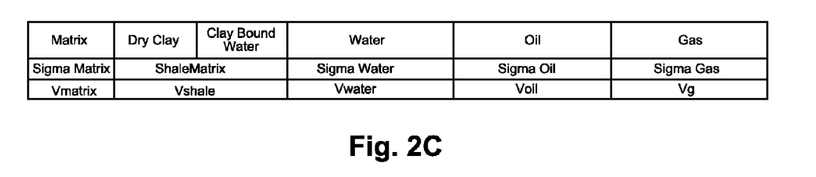

FIGS. 2A-2C show petrophysical models including a classical model, a two phase model related to a long detector measurement, and a three phase model related to a long detector measurement. FIG. 2A shows a classic model of a formation composed of solids and fluids. The solids include matrix and dry clay. The matrix of rock is the finer grained mass of material in which larger grains, crystals, or clasts are embedded. The fluids can include clay bound water, cap held water, free-water, oil, and gas.

FIG. 2B shows a petrophysical model in which the inelastic to capture ratio using a long detector can characterize fluids as liquids separate from gas. This inelastic to capture ratio using a long detector, providing a base case, may be able to be used to generate a gas saturation. Dry clay and clay bound water can be characterized as shale having a volume, $V_{sh}$, in addition to the matrix having a volume, $V_{matrix}$. Fluids can be characterized as liquids and gas having an effective porosity, where the total porosity includes the clay bound water.

FIG. 2C shows three phase evaluation in saline formation where oil and water density contrast are low. This model includes matrix, dry clay, clay bound water, water oil, and gas, which can be considered in terms of the volume and sigma of the mass content. Sigma is a thermal neutron capture cross section of a volume of matter. In this model, the matter content is characterized by a sigma of the matrix, a volume of the matrix, a sigma of shale, a volume of shale, a sigma of the water, a volume of the water, a sigma of the oil, a volume of the oil, a sigma of the gas, a volume of the gas. The shale is the combination of the dry clay and the clay bound water content of the formation.

Using the long detector, formation gas saturation and volume can be calculated. The long detector method provides a mechanism to evaluate gas verses the liquid phase of formation fluids, where the density contrast for the oil and water are low. For long source to detector spacing, average gamma transmission efficiency between inelastic gamma rays and capture gamma rays becomes similar during transport from the edge of a capture area to the detector. For the long detector, the ratio between the inelastic gate and the slow capture gate is the saturation gate (SATG). A gate is related to a count rate over a period of time. The long detector method using this ratio between the inelastic and capture gamma may be referred to as a SATG method. In conditions where there is sufficient contrast in sigma values of the oil and water (Salty), the SATG method and Sigma measurement results can be combined to resolve gas, oil, and water saturation/volumes.

Sigma is a property of a material, whose value is known for each of a variety of materials. For example, fresh water and oil have cross sections that are approximately equal at about 22 capture units. However, reservoirs can have high water salinity such that there is a significant contrast between the saline material and oil. In a high salinity formation, the SATG of the long detector is gas sensitive, but relatively insensitive to salinity. Using the long detector to generate SATG measurement provides a process to calculate gas saturation essentially independent of effects from liquids. With the gas saturation provided by the SATG measurements, the corresponding volume of the gas can be determined from knowing the porosity of the measured formation. The remaining fluid can be oil, some other form of liquid, or combinations thereof. Having measured gas independent of salinity using the long detector, a detector having a shorter distance to a corresponding neutron source can be used to determine the sigma of the saline material in a traditional salinity measurement. Based on these two measurements, the amount of water and amount of oil can be determined. This evaluation technique provides a mechanism to conduct a triple phase evaluation.

Figure 3:
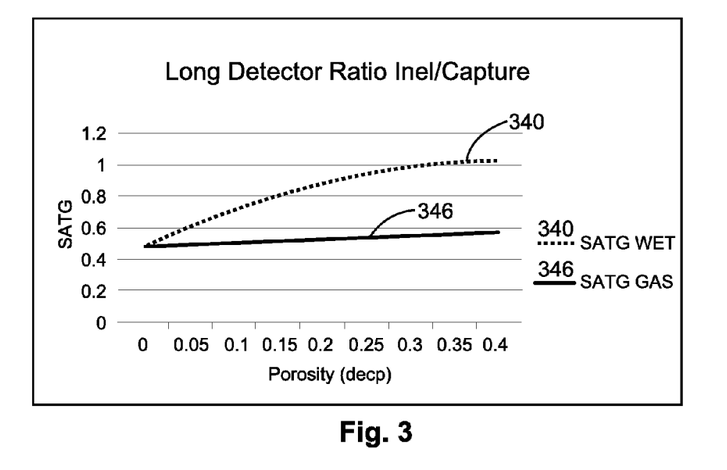
FIG. 3 shows an example of a saturation gate characterization for two phases, in accordance with various embodiments.

FIG. 3 shows an example of a SATG characterization for two phases. Long detector inelastic gamma counts, captured gamma counts, and their ratios can be characterized with respect to SATG responses to water and gas in fluid filled porosity rock. Curve 340 represents SATG values as a function of porosity for 100% water filled porosity rock. Curve 346 represents SATG values as a function of porosity for 100% gas filled porosity rock. Curves 340 and 346 form an envelope in which measured SATG values falling between curves 340 and 346 indicate a percentage of the formation containing a volume of gas. The SATG values for the gas curve forming the envelope are represented as SATGgas. The SATG values for the water curve forming the envelope are represented as SATGwet, where wet refers to water. The measured SATG values for fluid filled porosity rock are SATGmea. The percentage of the gas phases in water and gas filled porosity rock is the gas saturation, $S_g$, which can be described by equation (1) as:

$$S_g = \left(1 - \frac{SATGmea - SATGas}{SATGwet - SATGgas}\right) \quad (1)$$

Figure 4:
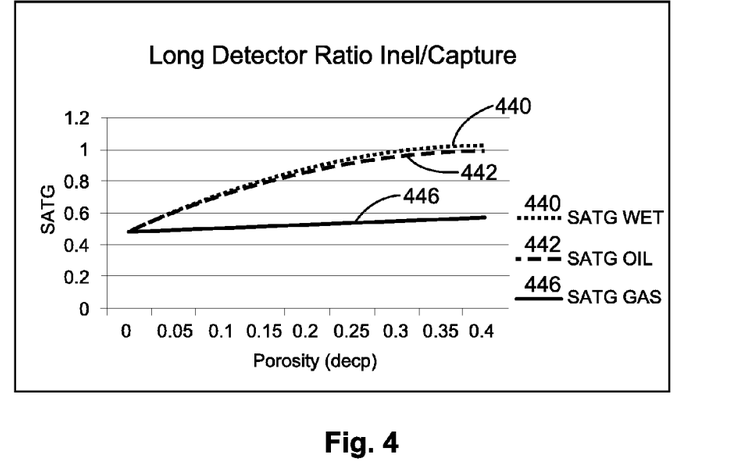
FIG. 4 shows an example of a saturation gate characterization for three phases, in accordance with various embodiments.

FIG. 4 shows an example of a SATG characterization for three phases. Long detector inelastic gamma counts, captured gamma counts, and their ratios can be characterized with respect to SATG responses to different fluids in fluid filled porosity rock. Curve 440 represents SATG values as a function of porosity for 100% water filled porosity rock. Curve 442 represents SATG values as a function of porosity for 100% oil filled porosity rock. Curve 446 represents SATG values as a function of porosity for 100% gas filled porosity rock. Where contrast in density of oil and water is low, their responses converge and can be considered as a single liquid phase, as can be seen in FIG. 4.

As can be seen in FIGS. 3 and 4, there are regions of the envelope that have relatively large area compared to regions on the opposite side of the envelope. With small fluctuations in accuracy of the measurement, the relative error from the large area can be significantly smaller than the relative error based on a small area region. A relative constraint can be generated to apply to the three-phase evaluation. For example, if porosity and the difference between salinity measurement versus the oil measurement is greater than, but not limited to, a selected value, then this relationship may be taken to provide acceptable accuracy. Equation (2) provides an example constraint, where the product of the porosity, $\phi^*$, for the liquid phase, and the contrast between the sigma of water (saline formation), $\Sigma_{water}$, and the sigma of oil, $\Sigma_{oil}$, is greater than three. Depending on the application, threshold values other than three can be used.

$$\phi^*(decp) \times (\Sigma_{water} - \Sigma_{Oil}) > 3 \quad \text{Acceptable Saturation-Eval} \quad (2)$$

Thus, equation (2) provides an example condition that allows for acceptable saturation accuracy of the oil and water phase.

As noted above, the long detector can provide measurements that provide the gas saturation in a measured formation. Sigma measurements can provide additional data to analyze the gas, water, and oil volume of the measured formation. The three phase response of a sigma measurement can be described by equation (3):

$$\Sigma_{meas} = \Sigma_{mat} V_{mat} + \Sigma_{sh} V_{sh} + \Sigma_g V_g + \Sigma_{oil} V_{oil} + \Sigma_w V_w \quad (3)$$

$\Sigma_{meas}$ is the measured sigma, which includes contributions from the matrix, shale, gas, oil, and water in the measured formation. $V_{mat}$ is the volume of the matrix and $\Sigma_{mat}$ is the sigma of the matrix. $V_{sh}$ is the volume of the shale and $\Sigma_{sh}$ is the sigma of the shale. $V_g$ is the volume of the gas and $\Sigma_{gas}$ is the sigma of the gas. $V_{oil}$ is the volume of the oil and $\Sigma_{oil}$ is the sigma of the oil. $V_w$ is the volume of the water and $\Sigma_w$ is the sigma of the water. Equation (3) can be rearranged to determine the volume of water in the measured formation, according to $$V_w = \frac{\Sigma_{meas} - \Sigma_{mat} V_{mat} - \Sigma_{sh} V_{sh} - \Sigma_{oil} V_{oil} - \Sigma_g V_g}{\Sigma_w - \Sigma_g}. \quad (4)$$

The mass balance equation of all the different material volumes in a rock is given by $$V_{mat} + V_{sh} + V_g + V_{oil} + V_w = 1 \quad (5)$$

The relevant volume of gas is the product of the gas saturation and the porosity of the measured formation. With the gas saturation calculated from the SATG process, the volume of gas $V_g$ can be calculated by the product of gas saturation and porosity $\Phi$ as $$V_g = S_g \times \Phi. \quad (6)$$

The three phase evaluation for the gas, oil, and water phases in the measured formation can be calculated from equations (4), (5), and (6). With data collected from the long detector inelastic/capture ratios measurements and the pulsed neutron sigma measurements, the volumes of gas, oil, and water phases are the three unknowns in the three equations (4), (5), and (6).

In various embodiments, a three phase evaluation process can utilize long detector gas detection and measurement. Such triple phase evaluation in high salinity formations can use pulsed neutron sigma and long detector inelastic/capture ratios measurements. This three phase evaluation process allows log measurement to be made at a faster speed to traditional neutron induced gamma spectral method. This three phase evaluation process can offer a simpler and more accurate method to alternative gas detection methods using ratios of more than one detector.

Figure 5:
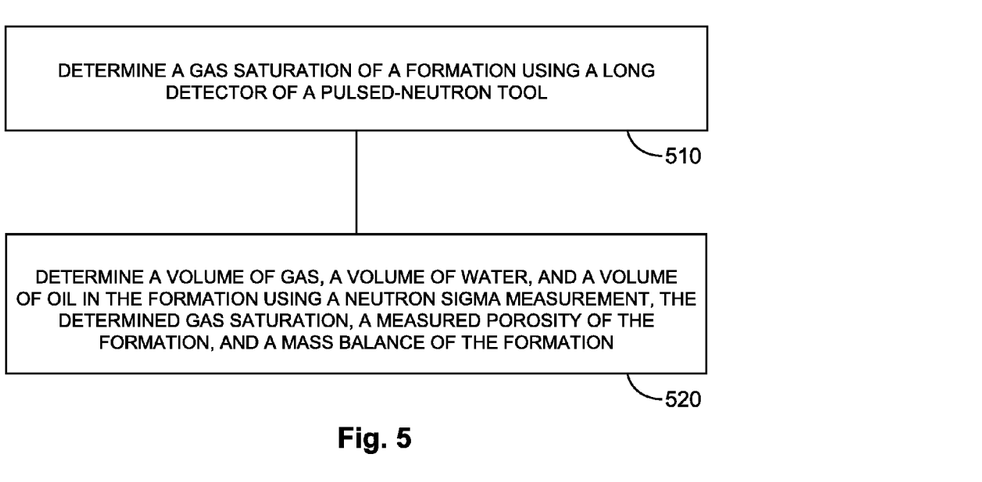
FIG. 5 shows features of an example method of determining water, gas, and oil content of a formation, in accordance with various embodiments.

FIG. 5 shows features of an example method of determining water, gas, and oil content of a formation. At 510, a gas saturation of a formation is determined using a long detector of a pulsed-neutron tool. Determining the gas saturation can include determining inelastic gamma count, capture gamma count, and a ratio between the inelastic gamma count and the capture gamma count using the long detector.

At 520, a volume of gas, a volume of water, and a volume of oil in the formation is determined using a neutron sigma measurement, the determined gas saturation, a measured porosity of the formation, and a mass balance of the formation. The volume of gas can be calculated by processing a product of the gas saturation and the measured porosity. The measured porosity can be determined using the pulsed-neutron tool. An acceptable accuracy of oil and water phases can be constrained by the measured porosity and a difference in terms of sigmas between a salinity measurement and an oil measurement being greater than a selected value. The selected value can be three. Other values for the accuracy constraint can be selected.

In various embodiments, components of a system operable to conduct triple phase evaluation of a formation, as described herein or in a similar manner, can be realized in software, hardware, or combinations of hardware and software based implementations. These implementations can include a machine-readable storage device having machine-executable instructions, such as a computer-readable storage device having computer-executable instructions, to determine a gas saturation of a formation from data collected using a long detector of a pulsed-neutron tool; and determine a volume of gas, a volume of water, and a volume of oil in the formation using a neutron sigma measurement, the determined gas saturation, a measured porosity of the formation, and a mass balance of the formation. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, and other electronic, magnetic, and/or optical memory devices.

Executed instructions can also include instructions to operate a tool having one or more pulsed-neutron sources and one or more detectors including the long detector to generate neutron pulses and detect gamma rays or other signals responsive to the neutron pulses to conduct the triple phase evaluation of the formation in accordance with the teachings herein. The instructions can include instructions to provide data to a processing unit such that the processing unit conducts one or more processes to evaluate signals, data, or signals and data. The instructions can include instructions to determine the gas saturation by an operation to determine inelastic gamma count, capture gamma count, and a ratio between the inelastic gamma count and the capture gamma count from using the long detector. The instruction can include instructions to calculate the volume of gas by processing a product of the gas saturation and the measured porosity. The operations include an operation to evaluate an acceptable accuracy of oil and water phases constrained by the measured porosity and a difference in terms of sigmas between a salinity measurement and an oil measurement being greater than a selected value. The selected value can be three. Other values for the accuracy constraint can be selected.

Figure 6:
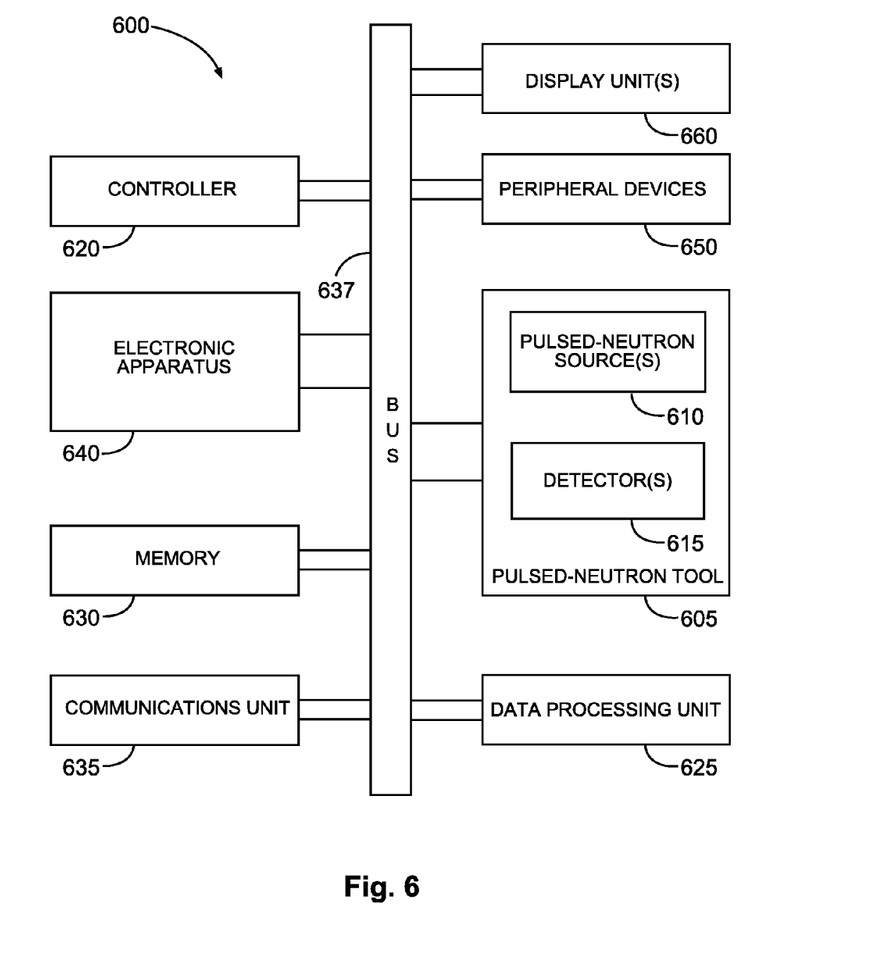
FIG. 6 depicts a block diagram of features of an example system operable to determine water, gas, and oil content of a formation, in accordance with various embodiments.

FIG. 6 depicts a block diagram of an embodiment of features of an example system 600 operable to determine water, gas, and oil content of a formation, as described herein or in a similar manner. The system 600 can include a pulsed-neutron tool 605 having an arrangement of pulsed-neutron source(s) 610 and detector(s) 615 that can be realized in a similar or identical manner to arrangements and processing discussed herein. The system 600 can be configured to operate in accordance with the teachings herein.

The system 600 can include a controller 620, a memory 630, an electronic apparatus 640, and a communications unit 635. The memory 630 can be structured to include a database. The controller 620, the memory 630, and the communications unit 635 can be arranged to operate as a processing unit to control operation of the pulsed-neutron source(s) 610 and the detector(s) 615 and to perform operations on the signals collected by the detector(s) 615 to conduct triple phase evaluation of the formation. A data processing unit 625, structured to conduct triple phase evaluation of the formation, can be implemented as a single unit or distributed among the components of the system 600 including electronic apparatus 640. The controller 620 and the memory 630 can operate to control activation of the pulsed-neutron source(s) 610 to generate neutron pulses. The controller 620 and the memory 630 can operate to control selection of the detector(s) 615 in the pulsed-neutron tool 605 and to manage processing schemes. The controller 620, the memory 630, and other components of the system 600 can be configured, for example, to operate similar to or identical to the components discussed herein or similar to or identical to any of methods discussed herein.

The communications unit 635 can include downhole communications for appropriately located sensors in a drilling operation. Such downhole communications can include a telemetry system. The communications unit 635 may use combinations of wired communication technologies and wireless technologies at frequencies that do not interfere with on-going measurements.

The system 600 can also include a bus 637, where the bus 637 provides electrical conductivity among the components of the system 600. The bus 637 can include an address bus, a data bus, and a control bus, each independently configured or in an integrated format. The bus 637 can be realized using a number of different communication mediums that allows for the distribution of components of the system 600. The bus 637 can include a network. Use of the bus 637 can be regulated by the controller 620.

In various embodiments, the peripheral devices 650 can include additional storage memory and other control devices that may operate in conjunction with the controller 620 and the memory 630. In an embodiment, the controller 620 can be realized as a processor or a group of processors that may operate independently depending on an assigned function.

The system 600 can include display unit(s) 660 as a distributed component on the surface at a drilling operation, which can be used with instructions stored in the memory 630 to implement a user interface to monitor the operation of the pulsed-neutron tool 605 or components distributed within the system 600. The user interface may be used to input parameter values for thresholds such that the system 600 can operate autonomously substantially without user intervention in a variety of applications. The user interface can also provide for manual override and change of control of the system 600 to a user. Such a user interface can be operated in conjunction with the communications unit 635 and the bus 637.

Figure 7:
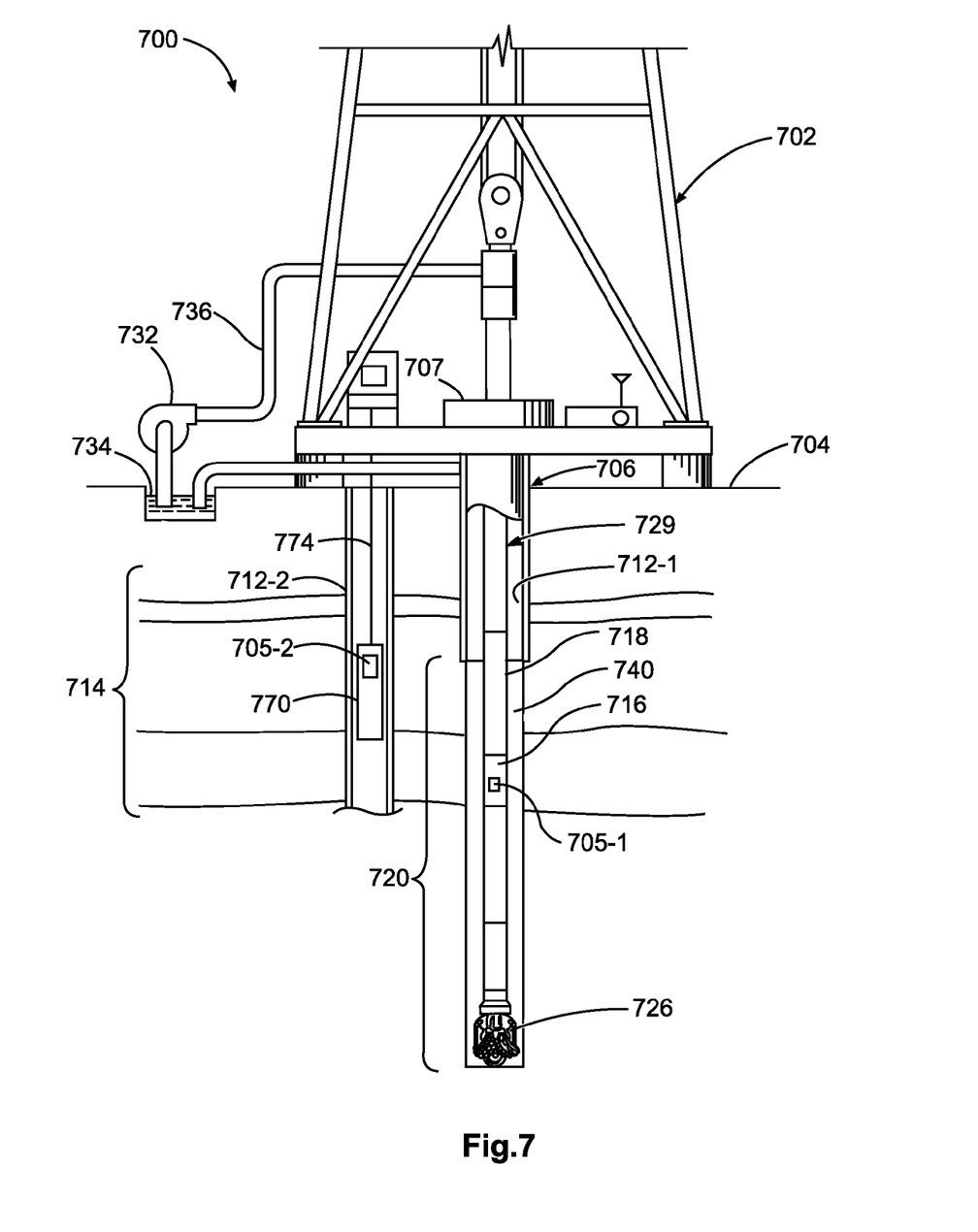
FIG. 7 depicts an example system at a drilling site, where the system is operable to determine water, gas, and oil content of a formation, in accordance with various embodiments.

FIG. 7 depicts an example embodiment of a system 700 at a drilling site, where the system is operable to determine water, gas, and oil content of a formation. The system 700 can include a tool 705-1, 705-2, or both 705-1 and 705-2 to conduct triple phase evaluation as taught herein. Tools 705-1 and 705-2 can be realized in a similar or identical manner to arrangements taught herein to conduct the triple phase evaluation.

System 700 can include a drilling rig 702 located at a surface 704 of a well 706 and a string of drill pipes, that is, drill string 729, connected together so as to form a drilling string that is lowered through a rotary table 707 into a wellbore or borehole 712-1. Drilling rig 702 can provide support for drill string 729. Drill string 729 can operate to penetrate rotary table 707 for drilling the borehole 712-1 through subsurface formations 714. Drill string 729 can include drill pipe 718 and a bottom hole assembly 720 located at the lower portion of drill pipe 718.

The bottom hole assembly 720 can include a drill collar 716 and a drill bit 726. Drill bit 726 can operate to create borehole 712-1 by penetrating the surface 704 and the subsurface formations 714. Bottom hole assembly 720 can include tool 705-1 attached to drill collar 716 to perform neutron measurements to conduct triple phase evaluation. Tool 705-1 can be structured for an implementation in a measure-while-drilling (MWD) system such as a logging-while-drilling (LWD) system. The housing containing tool 705-1 can include electronics to activate generation of neutron pulses from pulsed-neutron source(s) of tool 705-1 into a formation being analyzed and collect responses from detector(s) of tool 705-1. Such electronics can include a processing unit to provide analysis of water, gas, and oil content of the formation to the surface over a standard communication mechanism for operating in a well. Alternatively, electronics can include a communications interface to provide signals output by detector(s) of tool 705-1 to the surface over a standard communication mechanism for operating in a well, where these output signals can be analyzed at a processing unit at the surface to determine water, gas, and oil content of the formation.

During drilling operations, drill string 729 can be rotated by rotary table 707. In addition to, or alternatively, the bottom hole assembly 720 can also be rotated by a motor (e.g., a mud motor) that is located downhole. Drill collars 716 can be used to add weight to drill bit 726. Drill collars 716 also can stiffen the bottom hole assembly 720 to allow the bottom hole assembly 720 to transfer the added weight to drill bit 726, and in turn, assist drill bit 726 in penetrating surface 704 and subsurface formations 714.

During drilling operations, a mud pump 732 can pump drilling fluid (sometimes known by those of skill in the art as "drilling mud") from a mud pit 734 through a hose 736 into drill pipe 718 and down to drill bit 726. The drilling fluid can flow out from drill bit 726 and be returned to the surface 704 through an annular area 740 between drill pipe 718 and the sides of the borehole 712-1. The drilling fluid may then be returned to mud pit 734, where such fluid is filtered. In some embodiments, the drilling fluid can be used to cool drill bit 726, as well as to provide lubrication for drill bit 726 during drilling operations. Additionally, the drilling fluid may be used to remove subsurface formation 714 cuttings created by operating drill bit 726.

In various embodiments, tool 705-2 may be included in a tool body 770 coupled to a logging cable 774 such as, for example, for wireline applications. The tool body 770 containing the tool 705-2 can include electronics to activate generation of neutron pulses from pulsed-neutron source(s) of tool 705-1 into a formation being analyzed and collect responses from detector(s) of tool 705-2. Such electronics can include a processing unit to provide analysis of water, gas, and oil content of the formation to the surface over a standard communication mechanism for operating in a well. Alternatively, electronics can include a communications interface to provide signals output by magnetic sensor(s) of tool 705-2 to the surface over a standard communication mechanism for operating in a well, where these output signals can be analyzed at a processing unit at the surface to determine water, gas, and oil content of the formation. The logging cable 774 may be realized as a wireline (multiple power and communication lines), a mono-cable (a single conductor), and/or a slick-line (no conductors for power or communications), or other appropriate structure for use in the borehole 712.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
deploying a pulsed-neutron tool within a borehole, where the pulsed-neutron tool includes one or more neutron sources and one or more detectors including a long detector;
determining a gas saturation of a formation using the long detector; and
determining a volume of gas, a volume of water, and a volume of oil in the formation using a neutron sigma measurement, the determined gas saturation, a measured porosity of the formation, and a mass balance of the formation taking into consideration contributions from shale and matrix of rock in the neutron sigma measurement and the mass balance.

2. The method of claim 1, wherein determining the gas saturation includes determining inelastic gamma count, capture gamma count, and a ratio between the inelastic gamma count and the capture gamma count using the long detector.

3. The method of claim 1, wherein the volume of gas is calculated by processing a product of the gas saturation and the measured porosity.

4. A method comprising:
   deploying a pulsed-neutron tool within a borehole, where the pulsed-neutron tool includes one or more neutron sources and one or more detectors including a long detector;
   determining a gas saturation of a formation using the long detector; and
   determining a volume of gas, a volume of water, and a volume of oil in the formation using a neutron sigma measurement, the determined gas saturation, a measured porosity of the formation, and a mass balance of the formation taking into consideration contributions from shale and matrix of rock, wherein an acceptable accuracy of oil and water phases is constrained by the measured porosity and a difference in terms of sigmas between a salinity measurement and an oil measurement being greater than a selected value.

5. The method of claim 4, wherein the selected value is three.

6. A non-transitory machine-readable storage device having instructions stored thereon, which, when executed by one or more processors of a machine, cause the machine to perform operations, the operations comprising operations to:
   operate a pulsed-neutron tool within a borehole, where the pulsed-neutron tool includes one or more neutron sources and one or more detectors including a long detector;
   determine a gas saturation of a formation from data collected using the long detector; and
   determine a volume of gas, a volume of water, and a volume of oil in the formation using a neutron sigma measurement, the determined gas saturation, a measured porosity of the formation, and a mass balance of the formation taking into consideration contributions from shale and matrix of rock in the neutron sigma measurement and the mass balance.

7. The non-transitory machine-readable storage device of claim 6, wherein an operation to determine the gas saturation includes an operation to determine inelastic gamma count, capture gamma count, and a ratio between the inelastic gamma count and the capture gamma count from using the long detector.

8. The non-transitory machine-readable storage device of claim 6, wherein the instructions include instructions to calculate the volume of gas by processing a product of the gas saturation and the measured porosity.

9. A non-transitory machine-readable storage device having instructions stored thereon, which, when executed by one or more processors of a machine, cause the machine to perform operations, the operations comprising operations to:
   operate a pulsed-neutron tool within a borehole, where the pulsed-neutron tool includes one or more neutron sources and one or more detectors including a long detector;
   determine a gas saturation of a formation from data collected using the long detector; and
   determine a volume of gas, a volume of water, and a volume of oil in the formation using a neutron sigma measurement, the determined gas saturation, a measured porosity of the formation, and a mass balance of the formation taking into consideration contributions from shale and matrix of rock, wherein the operations include an operation to evaluate an acceptable accuracy of oil and water phases constrained by the measured porosity and a difference in terms of sigmas between a salinity measurement and an oil measurement being greater than a selected value.

10. The non-transitory machine-readable storage device of claim 9, wherein the selected value is three.

11. A system comprising:
    a pulsed-neutron tool deployed within a borehole, the pulsed-neutron tool having one or more pulsed-neutron sources and one or more detectors including a long detector;
    a control unit to control operation of the pulsed-neutron tool; and
    a data processing unit to determine a gas saturation of a formation from results of using the long detector and to determine a volume of gas, a volume of water, and a volume of oil in the formation using a neutron sigma measurement, the determined gas saturation, a measured porosity of the formation, and a mass balance of the formation taking into consideration contributions from shale and matrix of rock in the neutron sigma measurement and the mass balance.

12. The system of claim 11, wherein the data processing unit is operable to determine the gas saturation by determining a ratio between inelastic gamma count and capture gamma count from using the long detector.

13. The system of claim 11, wherein the data processing unit is operable to determine the volume of gas by calculating a product of the gas saturation and the measured porosity.

14. The system of claim 11, wherein the control unit and the data processing unit are structured as an integrated unit.

15. A system comprising:
    a pulsed-neutron tool deployed within a borehole, the pulsed-neutron tool having one or more pulsed-neutron sources and one or more detectors including a long detector;
    a control unit to control operation of the pulsed-neutron tool; and
    a data processing unit to determine a gas saturation of a formation from results of using the long detector and to determine a volume of gas, a volume of water, and a volume of oil in the formation using a neutron sigma measurement, the determined gas saturation, a measured porosity of the formation, and a mass balance of the formation taking into consideration contributions from shale and matrix of rock, wherein the data processing unit is operable to evaluate an acceptable accuracy of oil and water phases constrained by the measured porosity and a difference in terms of sigmas between a salinity measurement and an oil measurement being greater than a selected value.

16. The system of claim 15, wherein the selected value is three.

* * * * *